United States Patent [19]

Brown

[11] 4,416,292

[45] Nov. 22, 1983

[54] METHOD AND APPARATUS FOR DETERMINING THE NEUTRAL AXIS OF A FOOT OR THE LIKE

[76] Inventor: Dennis N. Brown, 1091 Fir Ave., Blaine, Wash. 98230

[21] Appl. No.: 294,307

[22] Filed: Aug. 19, 1981

[51] Int. Cl.³ ............................................... A61B 5/10
[52] U.S. Cl. ...................................... 128/779; 73/65; 33/174 D
[58] Field of Search ............. 128/774, 779, 782, 80 R, 128/80 DB, 581, 583–585; 73/1 E, 65; 33/3 R, 3 A, 3 B, 3 C, 6, 174 D; 12/115.2, 142 R; 82/45, DIG. 8; 3/2, 21, 30–35

[56] References Cited

U.S. PATENT DOCUMENTS

| | | | |
|---|---|---|---|
| 2,535,787 | 12/1950 | Darby | 33/174 D |
| 2,995,924 | 8/1961 | Karpovich | 73/65 |
| 3,358,373 | 12/1967 | Martin | 33/174 D |
| 3,587,296 | 6/1971 | Povoas | 73/65 |
| 3,890,958 | 6/1975 | Fister et al. | 73/65 X |
| 3,977,034 | 8/1976 | Brown | 12/142 R |
| 3,995,002 | 11/1976 | Brown | 267/13 |
| 4,060,869 | 12/1977 | Brown | 12/115.2 |
| 4,085,375 | 4/1978 | Galuschak et al. | 73/1 E X |
| 4,186,449 | 2/1980 | Horvath | 3/21 X |

FOREIGN PATENT DOCUMENTS 1383594 2/1975 United Kingdom ................ 128/782

OTHER PUBLICATIONS

"The Foot in Standing", *U.S. Armed Forces Medical Journal*; vol. X, No. 8; 8-1959, pp. 886–888.

*Primary Examiner*—Lee S. Cohen
*Assistant Examiner*—Angela D. Sykes
*Attorney, Agent, or Firm*—Blair, Brown & Kreten

[57] ABSTRACT

A method for determining the neutral axis of a foot or the like, as well as an apparatus therefore. The neutral axis can be conveniently defined as the orientation of the subtalar joint wherein its relationship to adjacent bones is such that there is no movement in that area. Consequently no loading is transferred to adjacent areas. The method includes placing a level indicator on the sinus tarsi portion of the foot and rotating the foot relative to the vertical axis defined by the leg until the indicator on the level is centered, indicative of the neutral position. The level structure includes a hinged wing attached at one extremity to the indicator and a tether so that in the preferred form the level indicator is disposed in substantially a horizontal plane. Disposition of the indicator on the patella is also contemplated as being a part of this invention for orienting the foot when it is covered by a boot or the like.

12 Claims, 9 Drawing Figures

U.S. Patent     Nov. 22, 1983     4,416,292
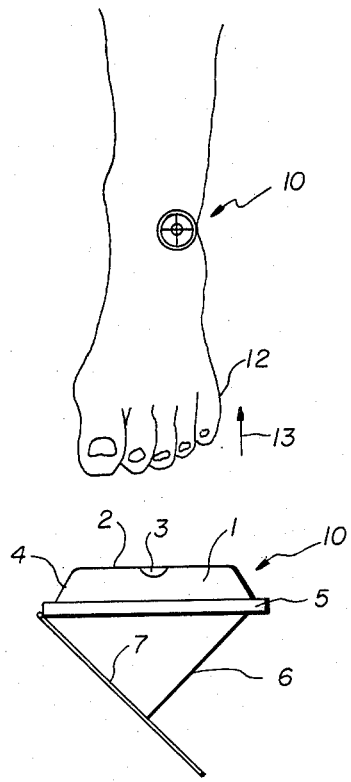
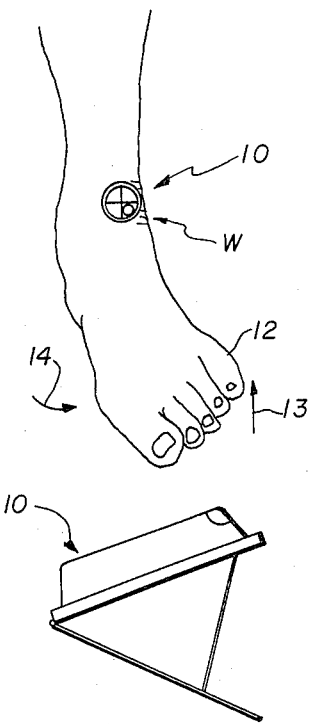
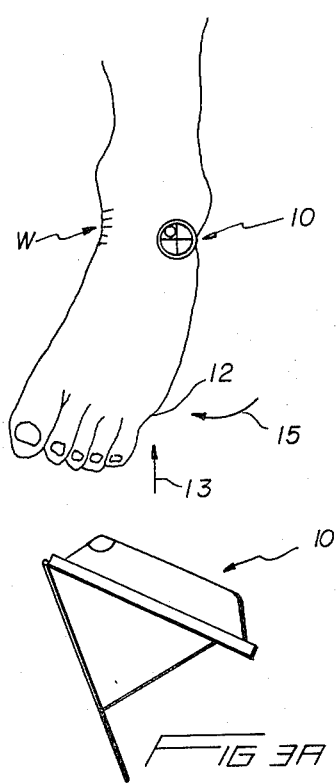
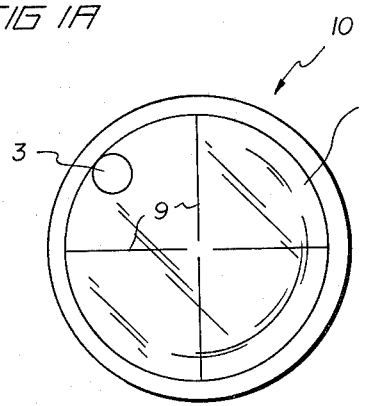
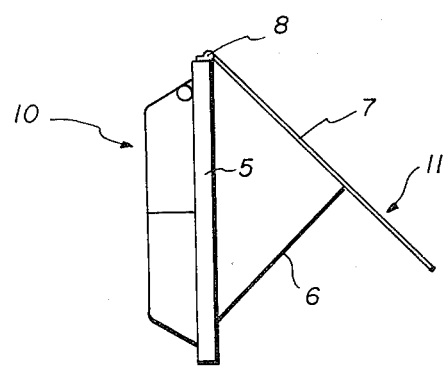
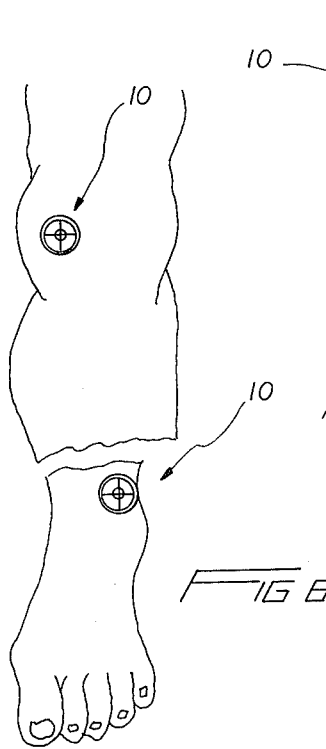

METHOD AND APPARATUS FOR DETERMINING THE NEUTRAL AXIS OF A FOOT OR THE LIKE

BACKGROUND OF THE INVENTION

The effectiveness of orthotic appliances is in large part determined by the skill of the practitioner and his associated ability to orient the foot to its bio-mechanically most efficient position prior to developing the orthosis. Unfortunately, in many instances, the neutral axis of the foot may be either initially somewhat difficult to find, or alternatively during the manipulative steps required in forming the orthosis, the orientation of the bones in the foot may shift slightly to place the foot out of the neutral position during the most critical molding phase.

The following patents reflect the state of the art of which applicant is aware in so far as these patents appear to be germane to the patent process, these patents directed to primarily the appliances associated with orthotic casting techniques, exhibiting the necessity of having the foot in the neutral axis position in order to provide the greatest benefits for the appliance wearer.

Brown—U.S. Pat. No. 3,977,034
Brown—U.S. Pat. No. 3,995,002
Brown—U.S. Pat. No. 4,060,869

While these references certainly teach the desirability of having the foot in a neutral position prior to and during the casting, none of these references teach nor render obvious the method and apparatus according to the present invention wherein the neutral axis can be initially determined in a facile manner and the neutral orientation can be maintained throughout the course of the casting by means of a visual indicator so that at all times until the casting is set, it is readily apparent when the foot is properly oriented relative to the vertical axis defined by the leg.

Further, the apparatus and method according to the instant application is directed to an invention which simply and efficiently locates the neutral axis of the foot, thereby enhancing and increasing the professionalism with which an orthotic appliance fitter can customize a shoe to a person, while concurrently reducing the skill level involved. This of course would tend to increase the likelihood of a proper fitting on an initial try.

SUMMARY AND OBJECTS OF THE INVENTION

Accordingly, this invention has as an object to provide a method for easily and conveniently locating the neutral axis of a foot.

It is yet another object of this invention to provide an apparatus associated with the method for the benefits attendant therewith.

It is still a further object of this invention to provide a device and method of the character described above which is inexpensive to manufacture, easily deployable upon the body portion of the person to be fitted, and extremely accurate in use.

A still further object of this invention is to provide a device and method of the character described above in which subsequent processes involving the foot can proceed providing a continuous indicator to encourge the correct orientation of the foot at all times. Heretofore, when molding was effected in providing an orthosis, a pressure step was required in which the impression of the foot is increased to provide a pattern having greater detail. However the time when the additional pressure is being applied, there is a possibility that the foot will rotate out of the neutral position thereby not providing a casting which reflects with total fidelity the desired purposes of the casting. Accordingly this invention has as an object to provide a device which continuously monitors the orientation of the foot as to its neutral position.

It is still a further object of this invention to provide a device and method of the character described above which, once the neutral axis has been determined on the foot, and an orthotic appliance is provided thereon, a boot or other device overlying the foot reduces accessibility to the foot, but the neutral axis can thereafter be found by placing the level indicator on the patella area of the knee so as to assist in further modifying the appliance with a boot or the like on the foot.

These and other objects will be made manifest when considering the following detailed specification when taken in conjunction with the appended drawing figures.

BRIEF DESCRIPTION OF THE DRAWING FIGURES

FIG. 1 is a front view of the apparatus according to the present invention in which the indicator reflects the foot in a neutral position;

FIG. 1a is a side view of the indicator itself during the orientation of FIG. 1;

FIG. 2 is a front view of the apparatus according to the present invention in which the foot is abducted/pronated showing the indicator in an off center position;

FIG. 2a is a side view thereof;

FIG. 3 is a front view of the apparatus according to the present invention with the foot adducted/supinated;

FIG. 3a is a side view of the level indicator or reflective of the situation of FIG. 3.

FIG. 4 is a top plan view of the level indicator according to the present invention;

FIG. 5 is a side view thereof; and

FIG. 6 teaches the use of placing the level indicators both on the foot and the knee area as will be explained hereinafter.

DESCRIPTION OF THE PREFERRED EMBODIMENT

Referring to the drawings now wherein like references numerals refer to like parts throughout the various drawing figures, reference numeral 10 is directed to the level indicator according to the present invention.

The level indicator as shown especially well in FIGS. 1a–3a, FIGS. 4 and 5 is generally formed as a substrate 5 having an upwardly extending frusto-conical hollow shell 1 defined by a perimeter wall 4 and planar top portion 2. The level is filled with a fluid as is well known in the level art, and a bubble 3 is allowed to remain within the container formed thereby so that movement of the bubble can reflect level and unlevel conditions. In order to provide an easy visual indicator of the level conditions, a marking is provided on the top face 2 of the level indicator, the marking 9 defining a set of cross hairs, the intersection of which corresponds with the center of the indicator.

In a preferred form of the invention, the level indicator is provided with a wing 7 hinged at one edge of the base 5, the hinge 8 being provided with a high degree of friction so that the orientation of the wing relative to the base 5 can be maintained in one position for purposes to be defined hereinafter. The limit of displacing the wing 7 from the base 5 can be controlled by means of a tether 6 so as to provide a natural stop beyond which the wing 7 is constrained. A back face of the wing 7 is provided with an adhesive 11 thereon so as to conveniently and firmly affix the wing on the sinus tarsi portion of the foot now to be described. Initially the level indicator is placed on the sinus tarsi area of the foot, which is an indentation just forward of the ankle. The adhesive means on a back face of the wing 7 is activated, and the level is placed on the sinus tarsi area is such a manner that one of the cross hairs extends in substantially a vertical direction. Thereafter, the level indicator base 5 is rotated upwardly until the level indicator is in substantially a horizontal plane, which is indicated by the bubble 3 crossing at or being near the second cross hair.

As is shown in FIG. 2, when the foot is abducted /pronated, skin creases are most noticable on the outside (lateral) foot position and stretches on the inside (medial). The sub-talar joint is now pronated. At this point, the bubble indicator shows that the neutral axis has not been maintained or is not yet found.

When the foot is adducted/supinated, the skin about the sub-talar joint creases on the inside (medial) foot position and stretches on the outside (lateral) and the sub-talar joint supinates. Notice the wrinkling W depicted in FIG. 3 compared to FIG. 2. Also, the level indicator reflects that the neutral axis has not been found. By way of contrast, when the sub-talar joint is neutral, the skin remains neutral on both sides of the sub-talar joint, and the level indicator shows that the bubble is substantially in the center of the indicator as defined by the cross hairs, and the sub-talar is now in a neutral mode.

In order to correctly rotate the foot about the sub-talar joint, vertical pressure is applied against the fifth metatarsal head 12 in order to dorsiflex the ankle (arrow in FIG. 1). In FIG. 2, in order to determine the neutral position, maintain vertical pressure against the fifth metatarsal head 12 as shown by the similar arrow 13, and a rotational force 14 will cause the joint to pronate as described above. FIG. 3 indicates that by maintaining the vertical pressure against the fifth metatarsal head 12 as shown by the direction of force arrow 13, and by providing a rotational force 15, the joint can than be allowed to supinate. In this manner, the neutral axis of the sub-talar joint can be determined.

Once the orientation of the sub-talar joint has been effected, a casting process similar to prior art appliances can be brought about with the neutral indicator maintaining its position on the foot, so that while the casting is setting up on the foot, there is no chance of having the foot inadvertently move from the neutral axis position.

Frequently however, once such a casting has been made, it is sometimes desirable to effect other modifications of the orthosis when that appliance is disposed within the boot, shoe, or other type of foot gear which does not necessarily lend itself to access of the foot area. In events such as these (for example when additional toe cresting is desired or modification of a boot tongue or for any other reason) once the neutral axis of the person's sinus tarsi has been determined, one can place the indicator or a second indicator on the patella of the knee, and orientation of the shin of that leg can induce the foot to return to the neutral axis position by using the indicator on the knee. In this manner, correct alignment between the knee and the foot through the sub-tarsal joint and the patella can further augment and assist the practitioner in custom orthotic appliance fitting. Additionally, in this manner, the body geometry of the knee can be provided with a similar level and using the points of reference of the other indicator, orientation of the entire body configuration can be beneficially effected.

Moreover, having thus described the invention, it should be apparent that numerous structural and method modifications are contemplated as being part of this invention, as set forth hereinabove, and as defined hereinbelow by the claims. For example, once the neutral axis has been developed, the axis can be locked into place by rotating the foot toward the knee and locking it in that position to provide a foot orientation which is less likely to wander from the neutral axis position than if the force just described were not applied.

What is claimed is:

1. A method for determining the neutral axis of a foot comprising, in combination:
   providing a level indicator on the sinus tarsi area of the foot,
   rotating the foot about a vertical axis defined by the leg of the foot,
   and fixing by holding the foot in a neutral position when the level indicator is centered.

2. The method of claim 1, including pushing the foot directly towards the leg after the level indicator is centered thereby locking the foot in a neutral position.

3. The method of claim 1 including rotating the foot by applying pressure against the fifth metatarsal head of the foot.

4. The method of claim 3 including orienting the level indicator in a substantially horizontal plane prior to seeking the neutral axis.

5. The method of claim 4 including providing a foldable wing on the level indicator adjacent a fold area,
   placing the wing on the sinus tarsi, and then rotating the level indicator to a horizontal plane.

6. The method of claim 5 including providing a tether between the level indicator and the wing remote from the fold area.

7. The method of claim 1 including placing a boot, shoe or the like on the foot after finding the neutral axis,
   placing the level indicator on the patella area of the knee and rotating the shoe, boot, or the like and therefore the foot,
   and noting when the level indicator is centered, thereby defining the neutral axis.

8. A level for finding the neutral axis of a foot comprising in combination:
   a level including a centering indicator,
   adhesive means on said level remote from said indicator for temporarily affixing said level to a person,
   and adjustable orientation means interposed between said level and said adhesive means to alter the angular relationship between said adhesive means and said level whereby said level can be moved once said adhesive means has been affixed to the person to initialize said level.

9. The device of claim 8 wherein said orientation means includes a wing, hinge means for connecting said wing to said indicator, said adhesive means for located on a face of said wing.

10. The device of claim 9 including tether means for connecting said wing to said indicator remote from said hinge means.

11. A level for finding the neutral axis of a foot comprising in combination:
a level including a centering indicator,
adhesive means on said level remote from said indicator whereby said level is adapted to be temporarily affixed to a person,
a wing and hinge for means connecting said wing means to said indicator, said adhesive means located on a face of said wing means.

12. The device of claim 11 including tether for connecting said wing to said indicator remote from said hinge means.

* * * * *